(12) United States Patent
Roncucci et al.

(10) Patent No.: US 8,664,382 B2
(45) Date of Patent: Mar. 4, 2014

(54) ANTIBACTERIAL COMPOSITIONS COMPRISING METAL PHTHALOCYANINE ANALOGUES

(75) Inventors: Gabrio Roncucci, Colle Val d'Elsa (IT); Donata Dei, San Gimignano (IT); Giacomo Chiti, Montemurlo (IT); Lia Fantetti, Florence (IT); Francesco Giuliani, Prato (IT); Giulio Jori, Padua (IT); Gian Maria Rossolini, Siena (IT)

(73) Assignee: Molteni Therapeutics S.r.l., Scandicci (FI) (IT)

( * ) Notice: Subject to any disclaimer, the term of this patent is extended or adjusted under 35 U.S.C. 154(b) by 1553 days.

(21) Appl. No.: 10/512,287

(22) PCT Filed: Apr. 17, 2003

(86) PCT No.: PCT/EP03/04080
§ 371 (c)(1),
(2), (4) Date: Oct. 25, 2004

(87) PCT Pub. No.: WO03/090744
PCT Pub. Date: Nov. 6, 2003

(65) Prior Publication Data
US 2005/0234032 A1    Oct. 20, 2005

(30) Foreign Application Priority Data
Apr. 25, 2002 (EP) ..................... 02009414

(51) Int. Cl.
*A01N 55/02* (2006.01)
*A61K 31/28* (2006.01)
*A61K 31/315* (2006.01)
*C07D 487/12* (2006.01)

(52) U.S. Cl.
USPC ............ 544/185; 514/494; 514/492

(58) Field of Classification Search
USPC .................. 544/185; 514/492, 494
See application file for complete search history.

(56) References Cited

U.S. PATENT DOCUMENTS

| 5,135,717 A | 8/1992 | Renzoni et al. |
| 5,965,598 A | 10/1999 | Roncucci et al. |
| 2006/0040914 A1 | 2/2006 | Roncucci et al. |

FOREIGN PATENT DOCUMENTS

| EP | 0 906 758 A1 | 4/1999 |
| EP | 0906758 A1 * | 4/1999 ............ A61K 31/555 |

(Continued)

OTHER PUBLICATIONS

Bertoloni et al. "Photosensitizing activity of water- and lipid-soluble phthalocyanines on *Escherichia coli*". FEMS Microbiology Letters. 1990. vol. 71. pp. 149-156.*

(Continued)

*Primary Examiner* — Benjamin Packard
(74) *Attorney, Agent, or Firm* — Wolf, Greenfield & Sacks, P.C.

(57) ABSTRACT

The present invention relates to pharmaceutical compositions comprising metal phthalocyanine analogues of formula (I) and metal chelating compounds having a good bioavailability and enhanced photoinactivation properties against Gram negative bacteria; and to their use for in vivo/ex vivo applications, such as blood and blood derivatives sterilization.

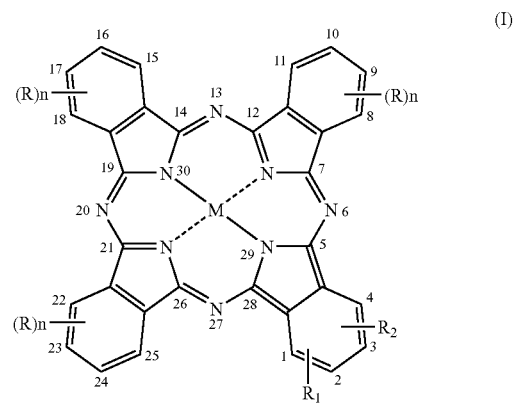

15 Claims, 6 Drawing Sheets

(56) References Cited

FOREIGN PATENT DOCUMENTS

| EP | 1 164 135 A1 | 12/2001 |
|---|---|---|
| WO | WO 01/96343 | 12/2001 |
| WO | WO 02/090361 | 11/2002 |

OTHER PUBLICATIONS

Bertoloni, G. et al., "Hematoporphyrin-Sensitized Photoinactivation of *Streptococcus Faecalis*," Photochem. & Photobio. 39(6):811 (1984).
Bertoloni, G. et al., "Photosensitizing Activity of Water—and Lipid-Soluble Phthalocyanines on *Escherichia coli*," FEMS Microbio. Lett. 71:149 (1990).
International Search Report, from PCT/EP03/04080, mailed Aug. 26, 2003.
Merchat, M. et al., "Meso-Substituted Cationic Porphyrins as Efficient Photosensitizers of Gram-Positive and Gram-Negative Bacteria," J. Photochem. & Photobio. 32:153 (1996).
Minnock, A. et al., "Photoinactivation of Bacteria. Use of a Cationic Water-Soluble Zinc Phthalocyanine to Photoinactivate Both Gram-Negative and Gram-Positive Bacteria," J. Photochem. & Photobio. 32:159 (1996).
Nitzan, Y. et al., "Inactivation of Gram-Negative Bacteria by Photosesitized Porphyrins," Photochem. & Photobio. 55(1):89 (1992).
Preliminary Examination Report, from PCT/EP03/04080, mailed Jun. 17, 2004.
Wohrle, D. et al., "A Simple Synthesis of 4,5-Disubstituted 1,2-Dicyanobenzenes and 2,3,9,10,16,17,23,24-Octasubstituted Phthalocyanines," Synthesis 194 (Feb. 1, 1993).
Bertoloni et al., "Hemotoporphyrin—Sensitized Photoinactivation of *Streptococcus faecalis*," *Photochemistry and Photobiology*, vol. 39, No. 6, pp. 811-816, (1984).
Bertoloni et al., "Photosensitizing activity of water- and lipid-solible phthalocyanines on *Escherichia coli*," FEMS Micriobiology Letters, vol. 71, pp. 149-156, (1990).
Louden, G. M., Organic Chemistry, Third Edition, Benjamin/Cummings: New York, 1995, p. 1, 344.
Minnock et al., "Photoinactivation of bacteria. Use of a cationic water-soluble zinc phthalocyanine to photoinactive both Gram-negative and Gram-positive bacteria," *J. of Photochem and Photobio B: Bio*, vol. 32, pp. 159-164, (1996).
Miyake et al., "Effects of Ethylenediaminetetraacetic Acid and Gentamicin on the Antibacterial Activity of Pyridone Carboxylic Acid Derivatives Against Gram-negative Bacilli," *J.Antimicrobial Chemotherapy*., vol. 17, pp. 327-332, (1986).
Nitzan et al., "Inactivation of Gram-Negative Bacteria by Photosensitized Porphyrins," *Photochemistry and Photobiology*, vol. 55, No. 1, pp. 89-96, (1992).
Joni, Giulio, "Tumour photosensitizers: approaches to enhance the selectivity and efficiency of photodynamic therapy," *Journal of Photochemistry and Photobiology*, vol. 36, pp. 87-93 (1996).
Merchat, M., et al., "Studies on the mechanism of bacteria photosensitization by meso-substituted cationic porphyrins," *Journal of Photochemistry and Photobiology*, vol. 35, pp. 149-157 (1996).
Notice of Allowance dated Aug. 30, 2010 for U.S. Appl. No. 10/532,278, Apr. 21, 2005, and Claims as Allowed.

* cited by examiner

ANTIBACTERIAL COMPOSITIONS COMPRISING METAL PHTHALOCYANINE ANALOGUES

FIELD OF THE INVENTION

The present invention relates to pharmaceutical compositions comprising the metal phthalocyanine analogues of formula (I) hereinafter reported and metal chelating compounds, having a good bioavailability and enhanced photodynamic properties, useful for the treatment of infectious diseases and for in vivolex vivo applications.

STATE OF THE ART

It is known that phthalocyanines are molecules able to produce singlet oxygen in good yields as a result of light irradiation and have therefore photoenhanced biocidal activity. The biocidal properties of such molecules, once properly directed, make these molecules extremely interesting for therapeutic applications. Zn(II)-phthalocyanines and other metal-phthalocyanines, having applications in is photodynamic therapy (PDT) and diagnosis, have been recently described in the U.S. Pat. No. 5,965,598, in the European Patent Applications No. 00112654.9, No. 01106411.0 and No. 01125770.6, all in the name of the Applicant, wherein this kind of compounds, their preparation processes and properties are also described.

Despite the very high efficiency showed by the above mentioned phthalocyanines, in particular by cationic phthalocyanines, against the majority of micro-organisms, Gram negative bacteria still remain more difficult to inactivate. Even with the most active compounds described in the above cited patents and patent applications photoinactivation rates for Gram negative bacteria are at least one order of magnitude lower when compared to the inactivation of Gram positive bacteria and yeast, by using the same photosensitizer and the same experimental conditions. On the other hand, non cationic compounds, having either a porphyrin or a phthalocyanine nucleus, do not show any efficacy against Gram negative unless administered in the presence of additional substances capable of altering the permeability of the outer membrane; $Ca^{2+}$ salts, Tris-EDTA, etc., have been used to this aim.

However, it is worth mentioning that the available literature report only spared and contradictory information in this regard. In fact, while G. Bertoloni et al. in *Photochem. Photobiol.* (1984) 39, 811-816; Y Nitzan et al. *Photochem. Photobiol.* (1992) 55, 89-96, found that *E. coli* pretreated with 0.7 or 5 μM EDTA show a retained resistance to porphyrin and light, thus concluding that Gram negative bacteria are photoresistant even after the treatment with EDTA, in another paper G. Bertoloni et al. have obtained different results by using Tris EDTA in combination with a neutral and an anionic phthalocyanines against Gram negative bacteria (G. Bertoloni et al., FEMS Microbiology Letters, (1990) 71, 149-156).

In view of the above said, the need is deeply felt to provide novel pharmaceutical compositions and/or delivery systems, having photodynamic enhanced properties and an increased efficiency, especially against the specific pathologies caused by Gram negative bacteria. In this way, any undesired side effects can be avoided by lowering the dosage of the phthalocyanine photosensitizer, while retaining a high bacterial photoinactivation efficiency.

SUMMARY OF THE INVENTION

The Applicant has now surprisingly found that phthalocyanines peripherally substituted in specific positions with cationic groups or with groups protonable at physiological pH, are particularly effective in inducing the in vitro photoinactivation in conjunction with metal chelating agents, in particular metal chelating agents having specificity for the $Ca^{2+}$ and $Mg^{2+}$ ions, such as 1,2-diaminocyclohexane-N,N,N',N'-tetraacetic acid (CDTA), diethylenetriamine-pentaacetic acid (DTPA) and ethylenediaminetetraacetic acid (EDTA).

A synergistic effect between the cationic phthalocyanine photosensitizers previously described by the Applicant and metal chelating agents has been observed. In fact, the efficacy of the cationic phthalocynine photosensitizers described in the previous patents and patent applications in the name of the Applicant, when used in combination with metal chelating agents, appears to be advantageously increased not only in comparison with a number of test photosentizers previously described, such as PPC (reported by A. Minnock et al. in *J. Photochem. Photobiol.* (1996) 32: 159-164) and $T_4MPyP$ (reported by M. Merchat et al. in *J. Photochem. Photobiol.* (1996) 32: 153-157), but also in comparison with the cationic phthalocyanines themselves, tested in the same experimental conditions.

Subject of the present invention are therefore the pharmaceutical compositions comprising at least a metal phthalocyanine analogue of formula (I)

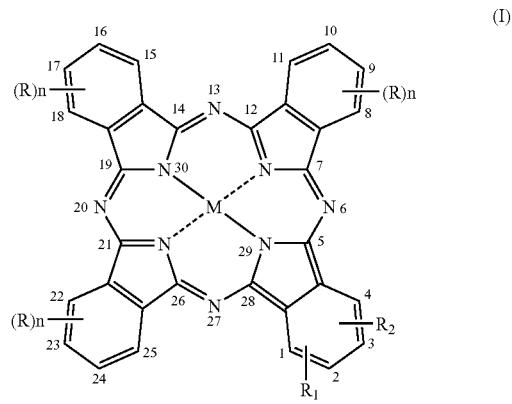

(I)

wherein
n is 0, 1 or 2;
M is chosen in the group consisting of Zn, $Si(OR_3)_2$ and $AlOR_3$ wherein $R_3$ is chosen in the group consisting of H and $C_{1-15}$ alkyl;
R is chosen from H and W, wherein W is represented by the group $(X)_pR_4$, wherein:
X is preferably chosen in the group consisting of O, S, $-NR_7$ and $-CH_2-$; and $R_4$ is

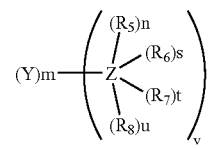

where:
Y is chosen in the group consisting of $C_{1-10}$ alkyl and phenyl, possibly substituted, or it forms with the Z group, to which it is bound, a saturated or unsaturated heterocycle, possibly substituted, which may contain up to two heteroatoms chosen in the group consisting of N, O and S;

Z is chosen in the group consisting of —N, —CH$_2$N and —CONHCH$_2$CH$_2$N;

R$_5$ and R$_6$, equal or different from one another, are chosen in the group consisting of C$_{1-15}$ alkyl and phenyl, or form with the Z group, to which they are bound, a saturated or unsaturated heterocycle, possibly substituted, which may contain up to two heteroatoms chosen in the group consisting of N, O and S;

R$_7$ and R$_8$, equal or different from one another, are chosen in the group consisting of H and C$_{1-15}$ alkyl;

m, n, p, s, t and u, independently from one another, are 0 or 1; and v is an integer comprised between 1 and 3;

R$_1$ and R$_2$, same or different from each other, are chosen from H, W and K, wherein W is as defined above, and K is selected from the group consisting of —COOH; —SH, —OH, —NH$_2$, —COCH$_2$Br, SO$_2$Cl, maleimide, hydrazide, phenol, imidate, and biotine, bound to the phthalocyanine nucleus, possibly through a suitable linker;

with the proviso that:

when n=0.
a) R$_1$=R$_2$=W in the position 1,4 or 2,3; or
b) R$_1$=H and R$_2$=W in the position 1 or 2; or
c) R$_1$=H and R$_2$=K in the position 1 or 2;

when n=1:
d) R$_1$=H, and R=R$_2$=W; or
e) R$_1$=H, R=W and R$_2$=K;

in both cases d) and e) R is in the positions 8(11), 15(18), 22(25), or 9(10), 16(17), 23(24); and R$_2$ is in the position 1(4) or 2(3);

when n=2:
f) R=R$_1$=R$_2$=W; or
g) R$_1$=H, R=W and R$_2$=K;

in both cases f) and g) R is in the positions 8,11,15,18,22,25, or 9,10,16,17,23,24; and in the case f) R$_1$ and R$_2$ are in the positions 1,4 or 2,3; whereas in the case g) R$_2$ is in the position 1(4) or 2(3);

in combination with at least a metal chelating agent.

Further subject of the invention is the use of the present pharmaceutical compositions in photodynamic therapy.

Features and advantages of the present formulations will be illustrated in detail in the following description.

BRIEF DESCRIPTION OF THE DRAWINGS

In the Figures described below the data obtained after irradiation of the cell suspensions, previously incubated with the present formulations, with 100 mW/cm$^2$ of red light, are indicated in the histograms by the white rectangles (the left bar in each group of two bars); the data obtained under the same conditions, but without the irradiation of light, are indicated by the dark rectangles (the right bar in each group of two bars).

DETAILED DESCRIPTION OF THE INVENTION

Figure 1:
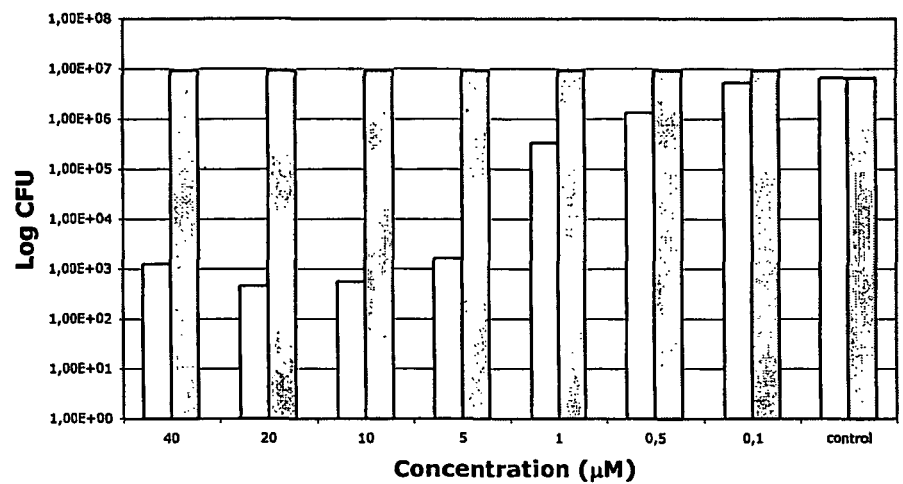
FIG. 1 shows the variation of CFU (colony forming units) of E. coli ATCC 25922 (Log CFU) vs. concentration (μM) of the compound {2,3,9,10,16,17,23,24-octa[3-(N,N,N-trimethylammonium)phenoxy]zinc(II) phthalocyanine}octaiodide (hereinafter referred to as "compound 1"), when a population of 6.6×10$^6$ CFU in 100 μL is incubated for 5 minutes with the above said compound.

The present invention allows to provide novel pharmaceutical compositions directed to the inactivation of Gram negative bacteria with enhanced physical-chemical and photodynamic properties thanks to the combination of the metal phthalocyanine analogues of formula (I) as above defined with at least a metal chelating agent.

According to the present invention Zn(II) and Si(IV) phthalocyanines are preferred. According to the invention, the definition "suitable linker" is intended in the sense commonly given to this definition in the field of protein and nucleic acid modification (S. S. Wang, Chemistry of Protein Conjugation and Cross-linking CRC Press Inc. 1993; G. T. Hermanson Bioconjugate Techniques Academic Press, 1996), i.e. an aliphatic moiety which acts as a spacer between the phthalocyanine nucleus and the biological macromolecules, in order to satisfy the desired sterical and/or structural requirements.

By saturated or unsaturated heterocycle possibly substituted, according to the present invention, the following are preferably meant: morpholine, piperidine, pyridine, pyrimidine, piperazine, pyrrolidine, pyrroline, imidazole, aniline, and julolidine (2,3,6,7-tetrahydro-1H,5H-pyrido[3,2,1-ij]quinoline).

According to the invention, the preferred products are those in which the group $(X)_pR_2$ includes substituents bearing tertiary or quaternary nitrogen. In particular, the said group $(X)_pR_4$, is preferably represented by:

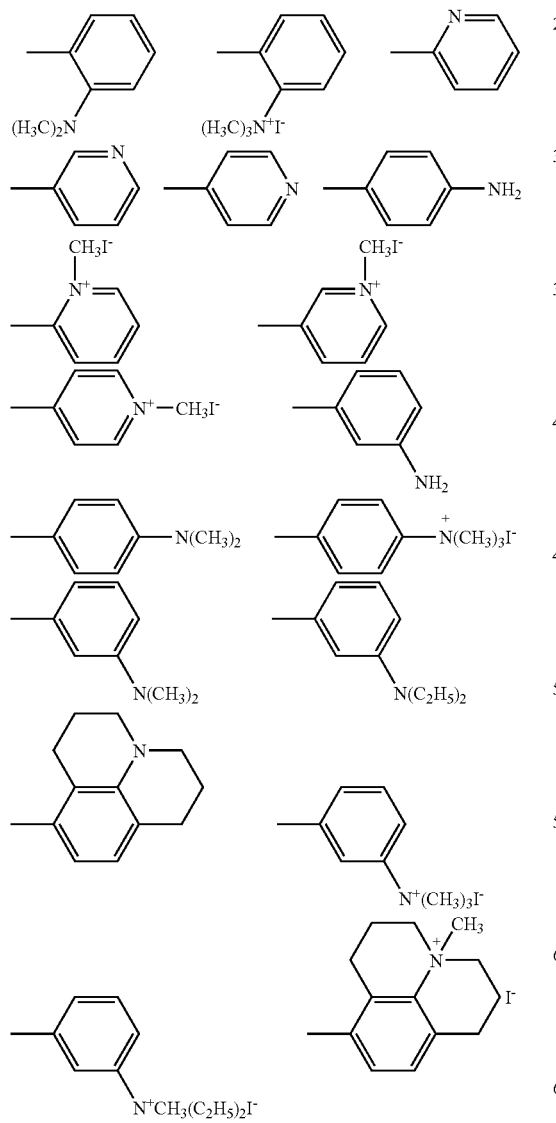

-continued

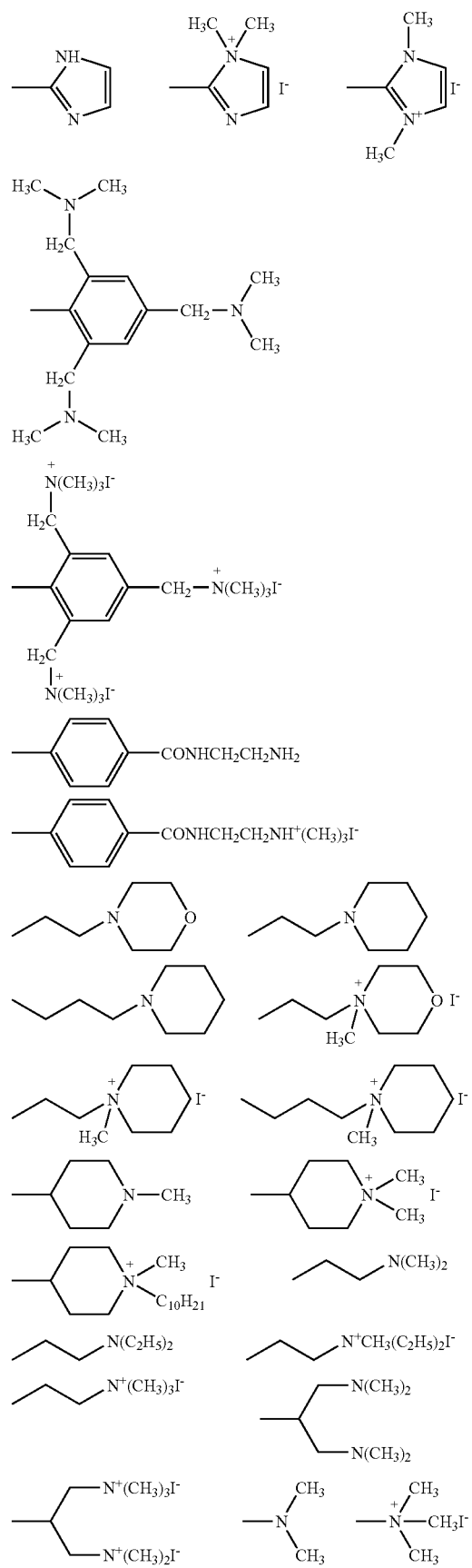

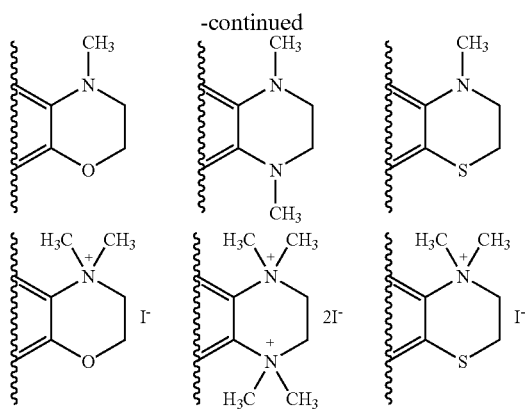

More preferably, the metal phthalocyanine analogues to be used in combination with metal chelating agents in the pharmaceutical compositions of the invention are defined by the following formulas:

{2,3,9,10,16,17,23,24-octa[3-(N,N,N-trimethylammonium)phenoxy]zinc(II) phthalocyanine}octaiodide (compound 1);

{2(3),9(10),16(17),23(24)-tetra[1,3-bis-(trimethylammonium)propyl-2-oxy]zinc(II) phthalocyanine}octaiodide (compound 2);

2(3),9(10),16(17),23(24)-tetra[1,3-bis-(dimethylamino)propyl-2-oxy]zinc(II) phthalocyanine (compound 3);

{2(3),9(10),16(17),23(24)-tetra[3-(N,N,N-trimethylammonium)phenoxy]zinc(II) phthalocyanine}tetraiodide (compound 4);

{2(3),9(10),16(17),23(24)-tetra[3-(N,N,N-diethylmethylammonium)phenoxy]zinc(II) phthalocyanine}tetraiodide (compound 5);

{1(4),8(11), 15(18),22(25)-tetra[3-(N,N,N-trimethylammonium)phenoxy]zinc(II) phthalocyanine}tetraiodide (compound 6);

{1(4),8(11),15(18),22(25)-tetra[3-(N,N,N-diethylmethylammonium)phenoxy]zinc(II) phthalocyanine}tetraiodide (compound 7);

{2,3,9,10,16,17,23,24-octa[3-(N,N,N-diethylmethylammonium)phenoxy]zinc(II) phthalocyanine}octaiodide (compound 8);

2(3),9(10),16(17),23(24)-tetra[4-(1-methylpiperidinil)oxy]zinc(II) phthalocyanine (compound 9);

1(4),8(11),15(18),22(25)-tetra[4-(1-methylpiperidinil)oxy]zinc(II) phthalocyanine (compound 10);

2(3),9(10),16(17),23(24)-tetra[2-(piperidin-1-yl)ethoxy]zinc(II) phthalocyanine (compound 11);

2(3),9(10),16(17),23(24)-tetra[2-(morpholin-4-yl)ethoxy]zinc(II) phthalocyanine (compound 12);

1(4),8(11),15(18),22(25)-tetra[2-(piperidin-1-yl)ethoxy]zinc(II) phthalocyanine (compound 13);

1,4,8,11,15,18,22,25-octa[2-(morpholin-4-yl)ethoxy]zinc(II) phthalocyanine (compound 14);

1,4,8,11,15,18,22,25-octa[3-(piperidin-1-yl)propoxy]zinc(II) phthalocyanine (compound 15);

1(4),8(11),15(18),22(25)-tetra[2-(morpholin-4-yl)ethoxy]zinc(II) phthalocyanine (compound 16);

1(4),8(11),15(18),22(25)-tetra[(1-methylpiperidin-2-yl)methoxy]zinc(II)phthalocyanine (compound 17);

{2(3),9(10),16(17),23(24)-tetra[N-(2-aminoethyl)benzamidoyl-4-oxy]zinc(II) phthalocyanine}tetra(trifluoroacetate) (compound 18);

{2(3),9(10),16(17),23(24)-tetra[2-(4-methylmorpholin-4-ium)ethoxy]zinc(II) phthalocyanine}tetraiodide (compound 19);

{2(3),9(10), 16(17),23(24)-tetra[2-(1-methylpiperidin-1-ium)ethoxy]zinc(II) phthalocyanine}tetraiodide (compound 20);

{1(4),8(11),15(18),22(25)-tetra[2-(1-methylpiperidin-1-ium)ethoxy]zinc(II) phthalocyanine}tetraiodide (compound 21);

{1(4),8(11),15(18),22(25)-tetra[2-(4-methylmorpholin-4-ium)ethoxy]zinc(II) phthalocyanine}tetraiodide (compound 22);

{2(3),9(10), 16(17),23(24)-tetra[4-(1-dimethylpiperidin-1-ium)oxy]zinc(II) phthalocyanine}tetraiodide (compound 23);

{2(3),9(10), 16(17),23(24)-tetra[3-(N,N,N-triethylmethylammonium)phenoxy]zinc(II) phthalocyanine}tetraiodide compound 24);

{2(3),9(10),16(17),23(24)-tetra[(N-methyl-2,3,6,7-tetrahydro-1H,5H-pyrido[3,2,1-ij]quinolinium-8-yl)oxy)]phthalocyanine}zinc(II) iodide (compound 25);

2,3,9,10,16,17,23,24-tetra[(N,N'-dimethyl)piperazo]zinc(II) phthalocyanine (compound 26);

2,3,9,10,16,17,23,24-octa[2-(N,N-diethylamino)ethylthio]zinc(II) phthalocyanine (compound 27);

{2,3,9,10,16,17,23,24-octa[3-(N,N,N-trimethylammonium)phenoxy]-dihydroxy Si(IV) phthalocyanine}octaiodide (compound 28);

{2,3,9,10,16,17,23,24-tetra[(N,N,N',N'-tetramethyl)piperazinediium]zinc(II) phthalocyanine}octaiodide (compound 29);

{2,3,9,10,16,17,23,24-octa[3-(N,N,N-trimethylammonium)phenylthio]zinc(II) phthalocyanine}octaiodide (compound 30);

{2,3,9,10,16,17,23,24-octa[3-(1-methylpiridin-ium)oxy]zinc(II) phthalocyanine}octaiodide (compound 31);

2,3,9,10,16,17,23,24-octa[2-(N,N-dimethylamino)ethylthio]zinc(II) phthalocyanine (compound 32);

{2,3,9,10,16,17,23,24-octa[2-(N,N,N-trimethylammonium)ethylthio]zinc(II) phthalocyanine}octaiodide (compound 33).

Pharmaceutically acceptable salts of the phthalocyanine compounds of the present invention, bearing basic substituents, include conventional acid addition salts, obtained by the addition of HCl, $H_3PO_4$, $H_2SO_4$, HBr, etc.

Additionally, salts obtained by reaction of the carboxylic function or acid groups within the phthalocyanine ring are within the scope of the present invention. Such salts include, for example, salts of carboxylic and sulfonic acid with amine derivatives, basic amino acids and inorganic bases.

The phthalocyanine compounds of the present invention can be prepared according to reaction schemes that are known in organic chemistry.

The present compounds of formula (I) included in the cases d) and f) may be prepared as described in U.S. Pat. No. 5,965,598, which we incorporate herewith by reference; whereas the present compounds of formula (I) included in cases c), e) and g) may be prepared as described in the International Patent Application No. PCT/EP02/03108, which we incorporate herewith by reference; the present compounds of formula (I) of cases a) and b) may be prepared as described in the European Patent Application No. EP 00112654.9, which we incorporate herewith by reference.

The phthalocyanine compounds indicated above as compounds 1-24 have been already disclosed in the above said Patent Applications, whereas the compounds indicated above as compounds 25-33 have been newly prepared as described in the following examples.

The present compositions comprise at least a metal chelating agent, preferably selected from the metal chelating agents having specificity for the $Ca^{2+}$ and $Mg^{2+}$ ions, such as 1,2-diaminocyclohexane-N,N,N',N'-tetraacetic acid (CDTA), diethylenetriamine-pentaacetic acid (DTPA), ethylenediamine-N,N,N',N'-tetraacetic acid (EDTA), and salts thereof.

More preferred compositions according to the invention are those comprising EDTA.

Photodynamic therapy using the phthalocyanine compounds formulated with the compound described in the present invention has a number of advantages. The phthalocyanine compounds themselves are minimally toxic in the unexcited state. Each phthalocyanine molecule can be repeatedly photoactivated and leads each time to cell-lethal events, that are the generation of singlet molecular oxygen or radicals. The half-life of singlet oxygen is such that the target cell is affected without the opportunity for migration of the lethal singlet oxygen to neighbouring healthy tissue cells. Singlet oxygen molecules target microorganism cell wall, or destroy intracellular structures, resulting in destruction of the target cell, without affecting chemical bonds in the cell DNA, at least at the doses which provide a complete photoinactivation. Destruction of target cell tissue commences promptly upon irradiation of the phthalocyanine compounds and ceases abruptly when irradiation is stopped and, due to the non interference with DNA, a development of resistance in microorganisms is unlikely. Photodynamic therapy with the compounds of the present invention is therefore selective and minimally toxic to healthy tissues. The produced singlet oxygen molecules that do not react rapidly with neighbouring molecules rapidly decay.

A variety of phototherapy and irradiation methodologies are known to those skilled in the art and can be used with the phthalocyanine metal chelating derivatives of the present invention. The time and duration of therapy and repetition of the irradiation treatment can be selected by the physician, according to known photodynamic therapy criteria. The dosage of the phthalocyanine and the metal chelating compound in the present compositions may be varied, according to the size and location of the target tissues which are to be destroyed and the method of administration. Generally, in the case of systemic (e.g. intravenous) administration of the photosensitizer, the dosage will be in the range between 0.1 and 20 mg of phthalocyanine compound per kilogram of body weight per day, more preferably in the range between 0.1 and 5.0 mg/kg.

In the case of topical deposition of the photosensitizer, the phthalocyriine dosage will be in the range between 0.1 and 100 µg of compound per $cm^2$ of tissue, more preferably in the range between 1 and 10 µg/$cm^2$.

The metal chelating compounds of the present invention may be administered in an amount ranging between 0.01 and 100 mg of the chelating compound per kilogram of body weight per day, and preferably in an amount ranging from 0.1 to 10 mg/Kg per day, in case of systemic administration, while a dosage between 0.1 and 100 µg/$cm^2$ per day, preferably in an amount ranging from 1 to 20 µg/$cm^2$, will be used in case of topical deposition.

For the treatment of infectious diseases, irradiation generally takes place not more than four days after systemic administration of the phthalocyanine compound. Usually, phototherapy begins approximately 10 hours to 24 hours after systemic administration of the photodynamic therapy agent. For dermatological infectious diseases, radiation therapy can commence immediately after topical application of is the phthalocyanine or at any desired time up to 24 hours later. Systemic application for treatment of dermatological diseases is followed by radiation usually 15 to 24 hours after systemic administration of the PDT agent. Exposure to non therapeutic light sources should be avoided immediately following phototherapy, to minimize light toxicity. Appropriate protection of the patient can be used, to limit the area affected by phototherapy.

Light sources suitable for the use in PDT are well known in the art and may vary from white light sources associated with appropriate filters to lasers tuned to the right wavelength. As noted above, preferred wavelengths are from 600 to 950 nm, preferably from about 650 to about 750 nm. The total amount of light which is applied to the affected area will vary with the treatment method used and with the location of the lesion. Generally, the amount of light is in the range of about 50 to 1000 J $cm^{-2}$, preferably in the range of 100 to 350 J $cm^{-2}$.

The present pharmaceutical compositions show valuable photodynamic characteristics and higher than the photosensitising agents previously described; these properties make them useful in photodynamic therapy (PDT) against bacterial, fungal and viral infections, in particular against Gram negative bacteria; as well as for sterilization of blood and blood derivatives, such as platelets and erythrocytes. In this case, the present compositions can be added directly to blood or blood derivatives, or previously bound to suitable matrix, according to known techniques and, thereafter, irradiated.

EXAMPLE 1

{2(3),9(10),16(17),23(24)-tetra[(N-methyl-2,3,6,7-tetrahydro-1H,5H-pyrido[3,2,1-ij]quinolinium-8-yl)oxy)] phthalocyanine}zinc(II) iodide (compound 25)

blue-green powder; formula: $C_{84}H_{80}I_4N_{12}O_4Zn$; UV-Vis (DMF) $\lambda_{max}$ (nm) 678 ($\epsilon$=174000 $M^{-1}$ $cm^{-1}$), 610, 357; $^1$H-NMR (200 MHz, DMSO-$d_6$) δ=9.50-9.38 (m, 4H), 9.20-8.95 (m, 4H), 7.95-7.82 (m, 4H), 7.46-7.42 (m, 8H), 4.10-3.91 (m, 16H), 3.55 (s, 12H), 3.30-3.20 (m, 16H), 2.72-2.60 (m, 8H), 2.40-2.30 (m, 8H); $^{13}$C-NMR (75 MHz, DMSO-$d_6$) δ 159.05, 158.94, 153.61, 153.48, 140.56, 134.25, 134.09, 130.06, 126.82, 126.76, 125.33, 123.35, 122.42, 120.87, 111.97, 111.75, 63.14, 62.71, 51.60, 23.84, 19.53, 16.07, 15.49; ESI-MS m/z 346 [(M-4I)$^{4+}$], 457 [(M-4I—$CH_3$)$^{3+}$], 678 [(M-4I-2$CH_3$)$^{2+}$], 1342 [(M-4I-3$CH_3$)$^+$].

EXAMPLE 2

2,3,9,10,16,17,23,24-tetra[(N,N'-dimethyl)piperazo] zinc(II) phthalocyanine (compound 26)

blue-green powder; formula: $C_{48}H_{48}N_{16}Zn$; UV-Vis (DMF) $\lambda_{max}$ (nm) 722; $^1$H-NMR (200 MHz, DMSO-$d_6$) δ= 8.37 (s, 8H), 3.69 (s, 16H), 3.43 (s, 24H); FAB-MS m/z 912 [$M^+$].

EXAMPLE 3

2,3,9,10,16,17,23,24-octa[2-(N,N-diethylamino) ethylthio]zinc(II) phthalocyanine (compound 27)

blue-green powder; formula: $C_{88}H_{120}N_{16}S_8Zn$.

EXAMPLE 4

{2,3,9,10,16,17,23,24-octa[3-(N,N,N-trimethylammonium) phenoxy]-dihydroxy Si(IV) phthalocyanine}octaiodide (compound 28)

blue-green powder; formula: $C_{104}H_{114}I_8N_{16}O_{10}Si$; UV-Vis (DMF) $\lambda_{max}$ (nm) 677, 609, 364; $^1$H-NMR (200 MHz, DMSO-d$_6$) δ=9.44 (s, 8H), 8.03 (bs, 8H), 7.85-7.65 (m, 16H), 7.50-7.40 (m, 8H), 3.68 (s, 72H); ESI-MS m/z 223 [(M-8I)$^{8+}$], 429 [(M-8I-4CH$_3$)$^{4+}$], 567 [(M-8I-5CH$_3$)$^+$], 843 [(M-8I-6CH$_3$)2$^+$], 1671 [(M-8I-7CH$_3$)$^+$].

EXAMPLE 5

{2,3,9,10,16,17,23,24-tetra[(N,N,N',N'-tetramethyl)piperazinediium]zinc(II) phthalocyanine}octaiodide (compound 29)

blue-green powder; formula: $C_{56}H_{72}I_8N_{16}Zn$; UV-Vis (DMF) $\lambda_{max}$ (nm) 722, 650, 372.

EXAMPLE 6

{2,3,9,10,16,17,23,24-octa[3-(N,N,N-trimethylammonium) phenylthio]zinc(II) phthalocyanine}octaiodide (compound 30)

blue-green powder; formula: $C_{104}H_{112}I_8N_{16}S_8Zn$; UV-Vis (DMF) $\lambda_{max}$ (nm) 707 (ε=146000 M$^{-1}$ cm$^{-1}$), 385, 635; $^1$H-NMR (200 MHz, DMSO-d$_6$) δ=9.46 (s, 8H), 8.31 (bs, 8H), 8.02-7.98 (m, 8H), 7.70 (dd, 8H, J=8.0 Hz), 7.57-7.54 (m, 8H), 3.71 (s, 72H).

EXAMPLE 7

{2,3,9,10,16,17,23,24-octa[3-(1-methylpiridin-ium)oxy] zinc(II) phthalocyanine}octaiodide (compound 31)

blue-green powder; formula: $C_{80}H_{64}I_8N_{16}O_8Zn$; UV-Vis (DMF) $\lambda_{max}$ (nm) 675; $^1$H-NMR (300 MHz, DMSO-d$_6$) δ= 9.56 (s, 8H), 9.33 (s, 8H), 8.93-8.91 (m, 8H), 8.67-8.64 (m, 8H), 8.27-8.22 (m, 8H), 4.40 (s, 24H); $^{13}$C-NMR (75 MHz, DMSO-d$_6$, selected data) δ=156.66, 153.35, 147.58, 142.06, 137.34, 136.80, 133.93, 129.74, 49.17.

EXAMPLE 8

2,3,9,10,16,17,23,24-octa[2-(N,N-dimethylamino) ethylthio]zinc(II) phthalocyanine (compound 32)

blue-green powder; formula: $C_{72}H_{88}N_{16}S_8Zn$.

EXAMPLE 9

{2,3,9,10,16,17,23,24-octa[2-(N,N,N-trimethylammonium) ethyithio]zinc(II) phthalocyanine}octaiodide (compound 33)

blue-green powder, formula: $C_{80}H_{112}I_8N_{16}S_8Zn$; UV-Vis (DMF) $\lambda_{max}$ (nm) 703, 631, 386; $^1$H-NMR (300 MHz, DMSO-d$_6$) δ=9.50 (s, 8H), 4.15-4.00 (m, 16H), 3.90-3.80 (m, 16H), 3.40 (s, 72H); $^{13}$C-NMR (75 MHz, DMSO-d$_6$, selected data) δ=153.7, 137.8, 137.1, 123.7, 64.1, 53.3, 26.9.

Biocidal Activity

The usefulness of the pharmaceutical compositions of the present invention has been evaluated through their activity against the Gram negative micro-organisms *Pseudomonas aeruginosa* PAO-1 and *E. coli* ATCC 25922. These microorganisms were used in the experiments in a stationary phase of growth.

The experimental protocol was the following:

The cell suspensions were diluted in an appropriate medium. Addition of an aliquot of stock solution of the composition to be tested to the cell suspension up to the intended final concentrations. Incubation in dark at 37° C. for 5 minutes. Irradiation (650≤λ≤850 nm; 50÷100 mW/cm2; 1÷10 minutes) of cell suspension for each dilution of the photosensitising composition.

FIG. 1 shows the photoinactivation of *E. coli* as a function of the concentration of the compound {2,3,9,10,16,17,23,24-octa[3-(N,N,N-trimethylammonium)phenoxy]zinc(II) phthalocyanine}octaiodide (compound 1). Compound 1 can afford a 4 log is reduction of the initial population, but a complete sterilization of the cell suspension cannot be obtained.

Figure 2:
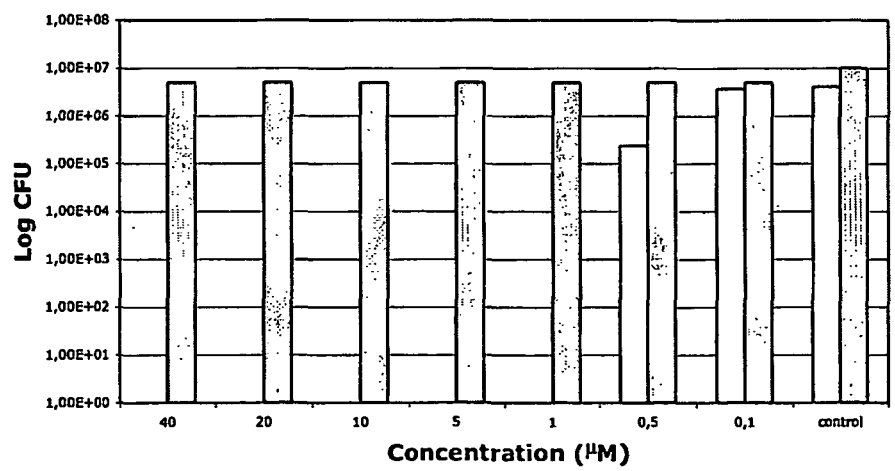
FIG. 2 shows the variation of CFU of E. coli ATCC 25922 (Log CFU) vs. concentration (μM) of the formulation according to the invention comprising the compound 1 in combination with EDTA 0.5 mM, when a population of 1.0×10$^7$ CFU in 100 μL is incubated for 5 minutes with the above said formulation.

The photoinactivation of *E. coli* caused by the compound 1 in combination with 0.5 mM of EDTA has been observed; as it can be seen in FIG. 2, the compound 1 in the presence of EDTA is able to sterilize completely the cell suspension at concentrations as low as 1 μM.

Figure 2A:
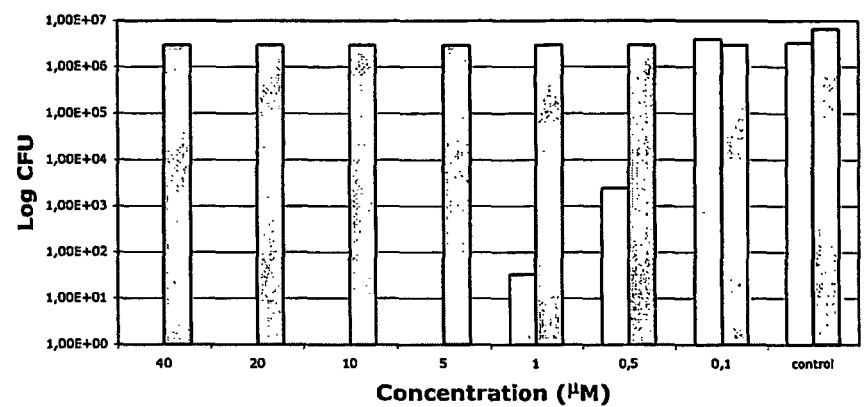
FIG. 2a shows the variation of CFU of E. coli ATCC 25922 (Log CFU) vs. concentration (μM) of the formulation according to the invention comprising the compound I in combination with CDTA 0.5 μM, when a population of 6.6×10$^6$ CFU in 100 μL is incubated for 5 minutes with the above said formulation.
Figure 2B:
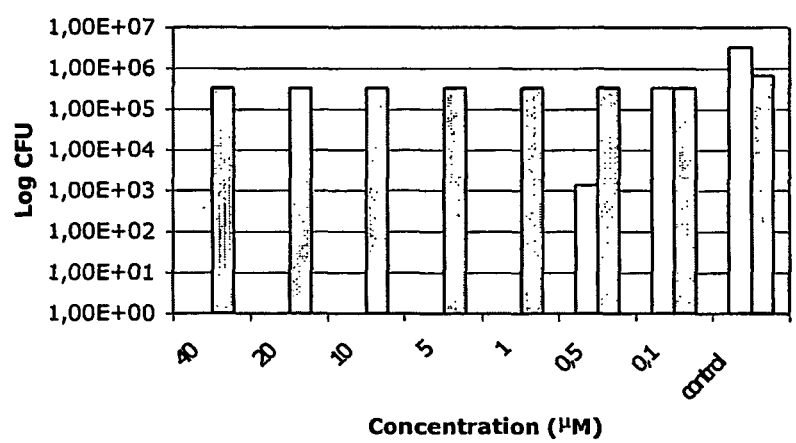
FIG. 2b shows the variation of CFU of E. coli ATCC 25922 (Log CFU) vs. concentration (μM) of the formulation according to the invention comprising the compound 1 in combination with DTPA 0.5 mM, when a population of 3.3×10$^6$ CFU in 100 μL is incubated for 5 minutes with the above said formulation.

Similar results can be also obtained by using CDTA or DTPA 0.5 mM (see FIGS. 2a and 2b).

Even more dramatic results can be obtained for the inactivation of *Pseudomonas aeruginosa*, a microorganism which is most refractory and difficult to inactivate.

Figure 3:
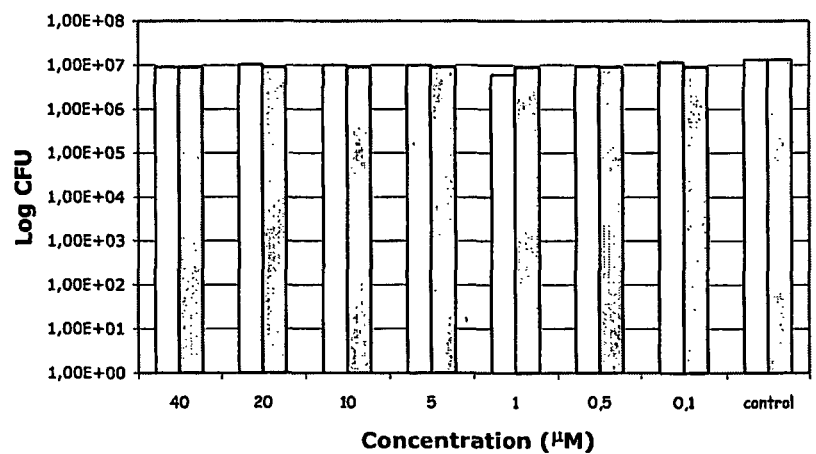
FIG. 3 shows the variation of CFU of Pseudomonas aeruginosa PAO-1 (Log CFU) vs. concentration (μM) of the present compound 1, when a population of 1.3×10$^7$ CFU in 100 μL is incubated for 5 minutes with the above said compound.
Figure 3A:
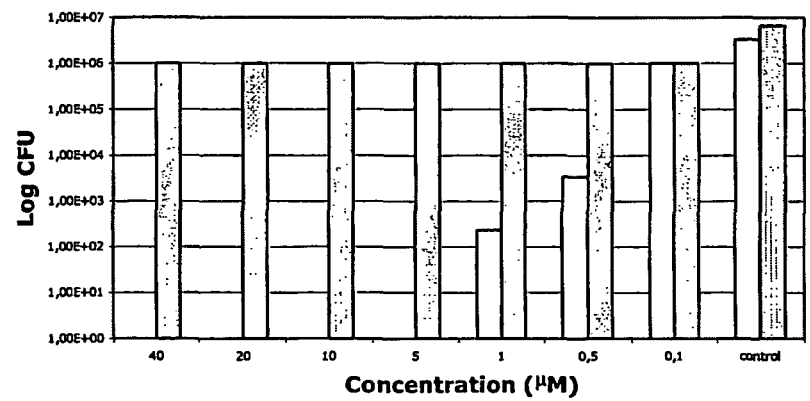
FIG. 3a shows the variation of CFU of P. aeruginosa PAO-1 (Log CFU) vs. concentration (μM) of the present formulation comprising the compound 1 in combination with EDTA 0.5 mM, when a population of 6.6×10$^6$ CFU in 100 μL is incubated for 5 minutes with the above said formulation.
Figure 3B:
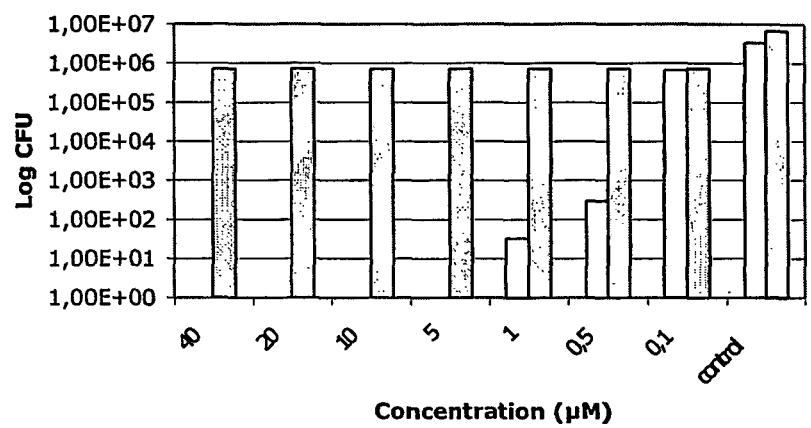
FIG. 3b shows the variation of CFU of P. aeruginosa PAO-1 (Log CFU) vs. concentration (μM) of the formulation of the invention comprising the compound 1 in combination with CDTA 0.5 mM, when a population of 6.6×10$^6$ CFU in 100 μL is incubated for 5 minutes with the above said formulation.
Figure 3C:
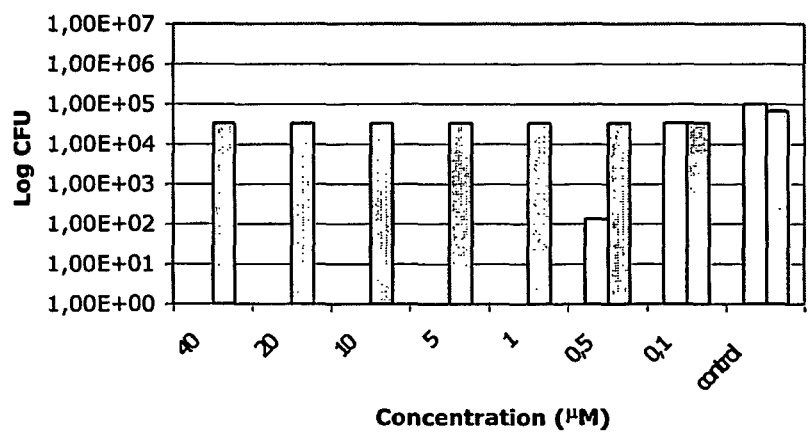
FIG. 3c shows the variation of CFU of P. aeruginosa PAO-1 (Log CFU) vs. concentration (μM) of the present formulation comprising the compound 1 in combination with DTPA 0.5 mM, when a population of 6.6×10$^6$ CFU in 100 μL is incubated for 5 minutes with the above said formulation.

In this case, compound 1 is not active up to 40 μM concentration (see FIG. 3), while by using EDTA, a concentration of 1 μM reduces the population by 5 log and a 5 μM concentration is able to sterilize the cell suspension (see FIG. 3a). Also in this case, similar results can be obtained with CDTA and DTPA (see FIGS. 3b and 3c).

Figure 4:
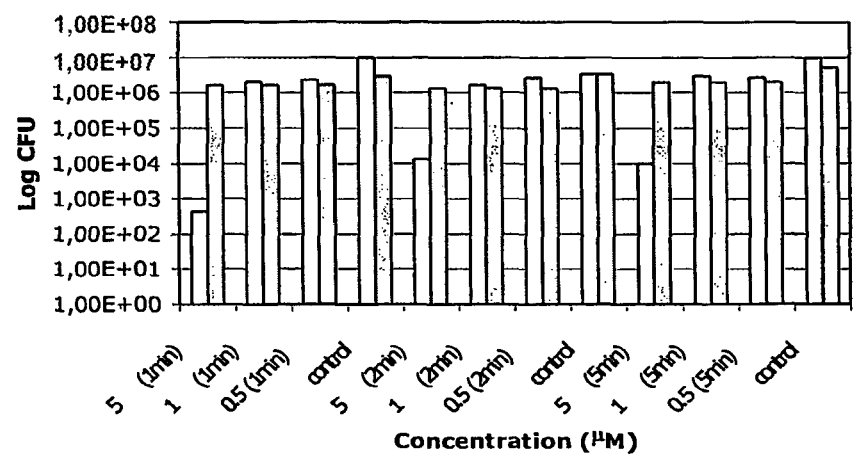
FIG. 4 shows the variation of CFU of P. aeruginosa PAO-1 (Log CFU) vs. concentration (μM) of the present formulation comprising the compound 1 in combination with EDTA 0.5 mM, at different irradiation times with 50 mW/cm$^2$ of red light, when a population of 1.0×10$^7$ CFU in 100 μL is incubated with the above said formulation.

It is worth noting that the inactivation can be performed by using lower fluence rates of light (50 mW/cm$^2$) and only 1 minute of irradiation (0.3 Jcm$^{-2}$) with 5 μM concentration is able to reduce the initial population by 4.5 log (see FIG. 4).

Figure 5:
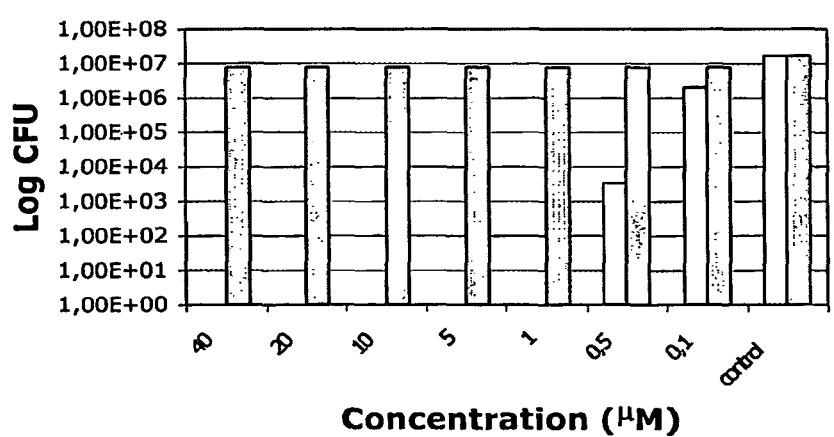
FIG. 5 shows the variation of CFU of E. coli ATCC 25922 (Log CFU) vs. concentration (μM) of the present formulation comprising the compound {2(3),9(10), 16(17),23(24)-tetra[1,3-bis-(trimethylammonium)propyl-2-oxy]zinc(II) phthalocyanine}octaiodide (hereinafter referred to as "compound 2") in combination with EDTA 0.5 mM, when a population of 6.6×10$^6$ CFU in 100 μL is incubated for 5 minutes with the above said formulation.
Figure 5A:
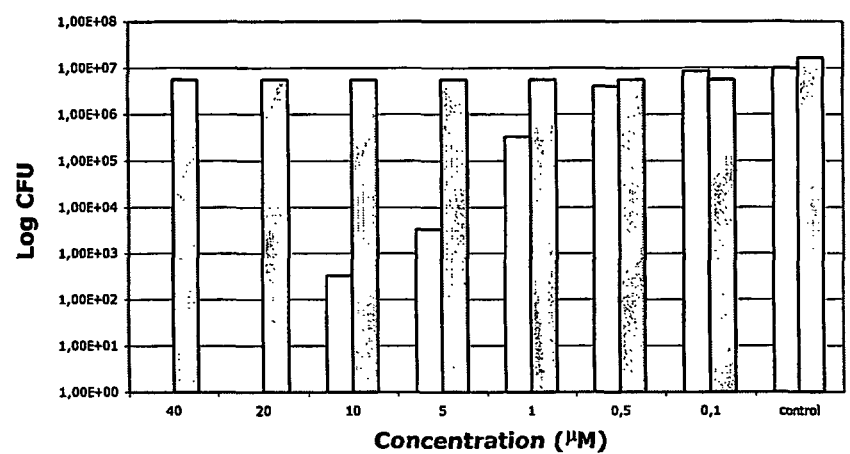
FIG. 5a shows the variation of CFU of E. coli ATCC 25922 (Log CFU) vs. concentration (μM) of the present formulation comprising the compound 2, when a population of 1.0×10$^7$ CFU in 100 μL is incubated for 5 minutes with the above said formulation.

Another example is, provided by the use of the compound {2(3),9(10),16(17),23(24)-tetra[1,3-bis-(trimethylammonium)propyl-2-oxy]zinc(II) phthalocyanine}octaiodide (compound 2) against *E. coli* with and without EDTA (see respectively FIGS. 5 and 5a). It is clearly shown that the presence of EDTA enables the reduction of the photosensitizer concentration necessary to sterilize the cell suspension from 20 μM to 1 μM.

Figure 6:
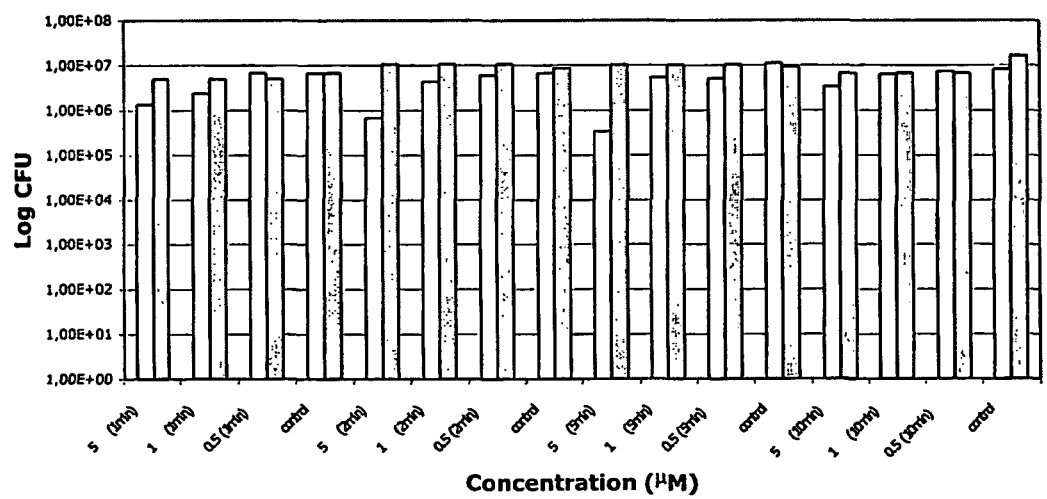
FIG. 6 shows the variation of CFU of P. aeruginosa PAO-1 (Log CFU) vs. concentration (μM) of a formulation comprising the compound 1 in combination with polymixine B sulphate 50 mM, at different irradiation times with 50 mW/cm$^2$ of red light, when a population of 1.0×10$^7$ CFU in 100 μL is incubated for 5 minutes with the above said formulation.

The synergistic effect of the present compositions is evident from the FIG. 6, wherein the results of a comparison experiment have been reported; in this experiment a phthalocyanine of formula (I) is used in combination with an enhancer commonly used, polymixine B sulphate, thus obtaining a scarce photoinactivation of the microorganisms, even at a concentration of 5 μM.

Pharmaceutical Formulations

Compositions as previously described may be administered by various routes, including parenterai or topical administration. In particular, the present compositions can be used either for topical treatment of skin or mucosae diseases, as well as for the ex vivo treatments, such as blood or blood derivatives sterilization.

Pharmaceutical compositions according to the present invention include solutions, liposome or microvesicle preparations, dispersions, ointments and other suitable topical dermatological preparations, or preparations suitable for ex vivo applications.

Such compositions may comprise pharmacologically acceptable diluents or excipients.

Parenteral Solutions

The photoactivatable phthalocyanines are generally used with additional solvents and adjuvants, to prepare solutions suitable for the in vivo or ex vivo administration. A number of solvents and co-solvents, that are miscible with water and suitable surfactants, can be used to achieve solutions for ex vivo application, assimilated to parenteral solutions and formulations. The most important solvents in this group are ethanol, polyethylene glycols of the liquid series and propylene glycol. A more comprehensive listing includes dimethyl sulfoxide, ethanol, glycerin, polyethylene glycol 300 and 400, propylene glycol, sorbitol, polyoxyethylene sorbitan, fatty acid esters such as laurate, palmitate, stearate and oleate, polyoxyethylated vegetable oil, sorbitan monopalmitate, 2-pyrrolidone, N-methyl-2-pyrrolidine, N-ethyl-2-pyrrolidine and tetrahydrofurfuryl alcohol.

Other additives may be necessary to enhance or maintain chemical stability and physiological suitability. Examples are antioxidants, chelating agents, inert gases, buffers and isotonicifiers.

Topical Formulations

The phthalocyanine and enhancers compounds of the present invention may be formulated for topical application in penetrating solvents or in the form of a lotion, cream, ointment or gel, containing a sufficient amount of the phthalocyanine compound to be effective for PDT.

Suitable penetrating solvents are those which will enhance percutaneous penetration of the phthalocyanine compound. Solvents having this property include dimethyl sulfoxide, 1-methyl-2-pyrrolidone, AZONE® (1-dodecylazacycloheptan-2-one), TRANSCUTOL® (ethyl diglycol or diethylene glycol monoethyl ether), lauric acid and esters, essential oils, propylene glycol, ethanol and PEG at various molecular weights. DMSO solutions containing 0-50 wt. % of water are particularly desirable.

Liposome or Microvesicle Preparations

Liposomes are microvesicles which encapsulate a liquid within lipid or polymeric membranes; the methods of preparing liposomes for both topical and parenteral (injectable) preparations are known in the art and can be used for the purposes of the present invention. The present compositions having overall lipophilic characteristics may be incorporated into liposome microvesicles and used in this form for both topical and ex vivo applications.

The invention claimed is:

1. Pharmaceutical compositions comprising at least a metal phthalocyanine analogue of formula (I)

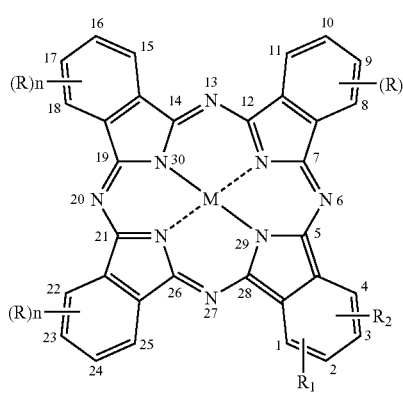

wherein n is 0, 1 or 2;

M is chosen in the group consisting of Zn, $Si(OR_3)_2$ and $AlOR_3$ wherein $R_3$ is chosen in the group consisting of H and $C_{1-15}$ alkyl;

R is chosen from H and W, wherein W is represented by the group $(X)_pR_4$, wherein:

X is chosen in the group consisting of O, S, —$NR_7$ and —$CH_2$—;

and $R_4$ is

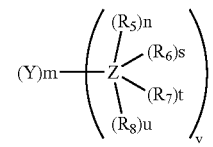

where:

Y is chosen in the group consisting of $C_{1-10}$ alkyl and phenyl, or it forms with the Z group, to which it is bound, a saturated or unsaturated heterocycle selected from the group consisting of: morpholine, piperidine, pyridine, pyrimidine, piperazine, pyrrolidine, pyrroline, imidazole, julolidine (2,3,6,7-tetrahydro-1H, 5H-pirido[3,2,1-Ij] quinoline;

Z is chosen in the group consisting of —N, —$CH_2N$ and —$CONHCH_2CH_2N$;

$R_5$ and $R_6$, equal or different from one another, are chosen in the group consisting of $C_{1-15}$ alkyl and phenyl, or form with the Z group, to which they are bound, a saturated or unsaturated heterocycle selected from the group consisting of: morpholine, piperidine, pyridine, pyrimidine, piperazine, pyrrolidine, pyrroline, imidazole, julolidine (2,3,6,7-tetrahydro-1H,5H-pirido[3,2,1-Ij] quinoline;

$R_7$ and $R_8$, equal or different from one another, are chosen in the group consisting of H and $C_{1-15}$ alkyl;

m, n, p, s, t and u, independently from one another, are 0 or 1; and v is an integer comprised between 1 and 3;

$R_1$ and $R_2$, same or different from each other, are chosen from H, W and K, wherein W is as defined above, and K is selected from the group consisting of —COOH, —SH, —OH, —$NH_2$, —$COCH_2Br$, $SO_2Cl$, maleimide, hydrazide, phenol, imidate, and biotine, bound to the phthalocyanine nucleus, either directly or through an aliphatic moiety which acts as a spacer;

with the proviso that:

when n=0:

a) $R_1$=$R_2$=W in the position 1, 4 or 2,3; or b) $R_1$=H and $R_2$=W in the position 1 or 2; or c) $R_1$=H and $R_2$=K in the position 1 or 2;

when n=1:

d) $R_1$=H, and R=$R_2$=W; or e) $R_1$=H, R=W and $R_2$=K;

in both cases d) and e) R is in the positions 8(11), 15(18), 22(25), or 9(10), 16(17), 23(24); and $R_2$ is in the position 1(4) or 2(3);

when n=2:

f) R=$R_1$=$R_2$=W; or g) $R_1$=H, R=W and $R_2$=K;

in both cases f) and g) R is in the positions 8,11,15,18, 22,25, or 9,10,16,17,23,24; and in the case f) $R_1$ and $R_2$ are in the positions 1, 4 or 2,3; whereas in the case g) $R_2$ is in the position 1(4) or 2(3);

in combination with at least a metal chelating agent.

2. The pharmaceutical compositions according to claim 1, wherein M is Zn or Si(OR$_3$)$_2$, where R$_3$ is defined as above in claim 1.

3. The pharmaceutical compositions according to claim 1, wherein the group (X)$_p$R$_4$ is chosen in the group consisting of:

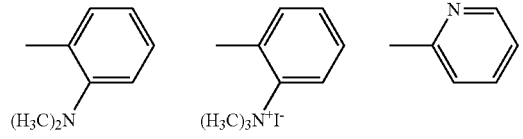

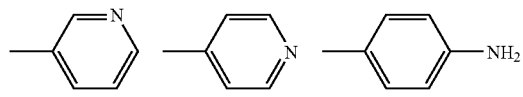

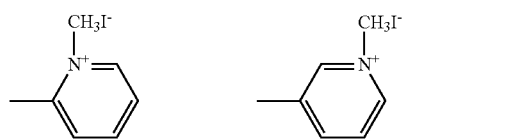

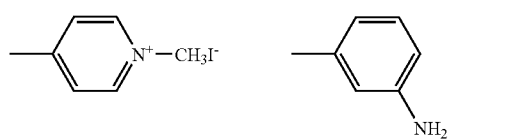

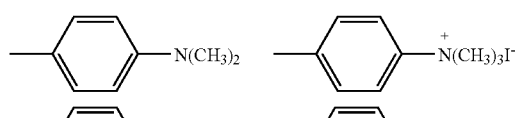

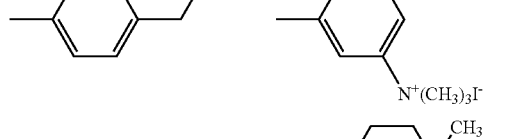

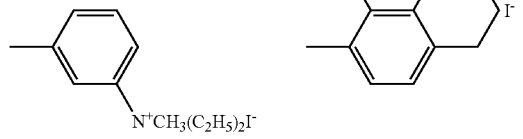

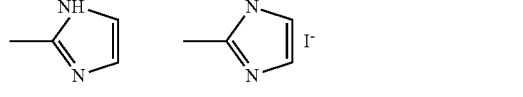

-continued

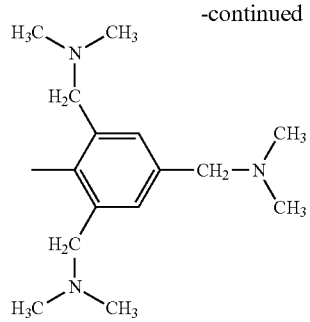

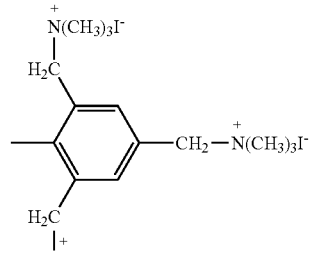

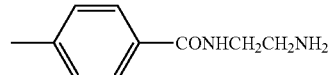

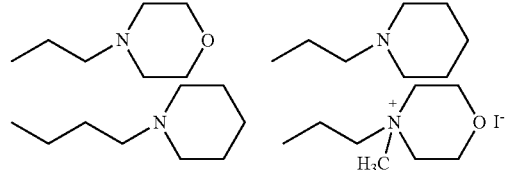

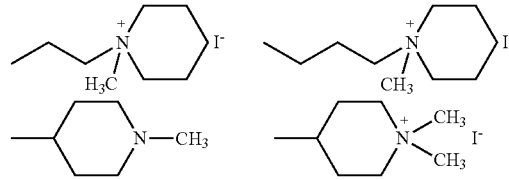

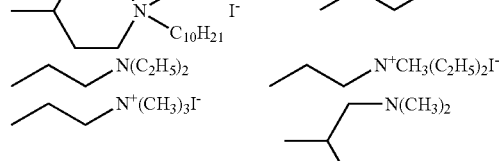

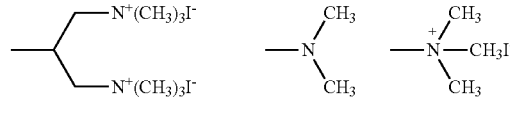

4. The pharmaceutical composition according to claim 1, wherein the said metal phthalocyanine analogue is defined by the following formulas:

{2,3,9,10,16,17,23,24-octa[3-(N,N,N-trimethylammonium)phenoxy]zinc(II) phthalocyanine}octaiodide (compound 1);

{2(3),9(10),16(17),23(24)-tetra[1,3-bis-(trimethylammonium)propyl-2-oxy]zinc(II) phthalocyanine}octaiodide (compound 2);

2(3),9(10),16(17),23(24)-tetra[1,3-bis-(dimethylamino) propyl-2-oxy]zinc(II) phthalocyanine (compound 3);

{2(3),9(10),16(17),23(24)-tetra[3-(N,N,N-trimethylammonium)phenoxy]zinc(II) phthalocyanine}tetraiodide (compound 4);

{2(3),9(10),16(17),23(24)-tetra[3-(N,N,N-diethylmethylammonium)phenoxy]zinc(II) phthalocyanine}tetraiodide (compound 5);

{1(4),8(11),15(18),22(25)-tetra[3-(N,N,N-trimethylammonium)phenoxy]zinc(II) phthalocyanine}tetraiodide (compound 6);

{1(4),8(11),15(18),22(25)-tetra[3-(N,N,N-diethylmethylammonium)phenoxy]zinc(II) phthalocyanine}tetraiodide (compound 7);

{2,3,9,10,16,17,23,24-octa[3-(N,N,N-diethylmethylammonium)phenoxy]zinc(II) phthalocyanine}octaiodide (compound 8);

2(3),9(10),16(17),23(24)-tetra[4-(1-methylpiperidinil)oxy]zinc(II) phthalocyanine (compound 9);

1(4),8(11),15(18),22(25)-tetra[4-(1-methylpiperidinil)oxy]zinc(II) phthalocyanine (compound 10);

2(3),9(10),16(17),23(24)-tetra[2-(piperidin-1-yl)ethoxy]zinc(II) phthalocyanine (compound 11);

2(3),9(10),16(17),23(24)-tetra[2-(morpholin-4-yl)ethoxy]zinc(II) phthalocyanine (compound 12);

1(4),8(11),15(18),22(25)-tetra[2-(piperidin-1-yl)ethoxy]zinc(II) phthalocyanine (compound 13);

1,4,8,11,15,18,22,25-octa[2-(morpholin-4-yl)ethoxy]zinc(II) phthalocyanine (compound 14);

1,4,8,11,15,18,22,25-octa[3-(piperidin-1-yl)propoxy]zinc(II) phthalocyanine (compound 15);

1(4),8(11),15(18),22(25)-tetra[2-(morpholin-4-yl)ethoxy]zinc(II) phthalocyanine (compound 16);

{2(3),9(10),16(17),23(24)-tetra[N-(2-aminoethyl)benzamidoyl-4-oxy]zinc(II) phthalocyanine}tetra(trifluoroacetate) (compound 18);

{2(3),9(10),16(17),23(24)-tetra[2-(4-methylmorpholin-4-ium)ethoxy]zinc(II) phthalocyanine}tetraiodide (compound 19);

{2(3),9(10),16(17),23(24)-tetra[2-(1-methylpiperidin-1-ium)ethoxy]zinc(II) phthalocyanine}tetraiodide (compound 20);

{1(4),8(11),15(18),22(25)-tetra[2-(1-methylpiperidin-1-ium)ethoxy]zinc(II) phthalocyanine}tetraiodide (compound 21);

{1(4),8(11),15(18),22(25)-tetra[2-(4-methylmorpholin-4-ium)ethoxy]zinc(II) phthalocyanine}tetraiodide (compound 22);

{2(3),9(10),16(17),23(24)-tetra[4-(1-dimethylpiperidin-1-ium)oxy]zinc(II) phthalocyanine}tetraiodide (compound 23);

{2(3),9(10),16(17),23(24)-tetra[3-(N,N,N-triethylmethylammonium)phenoxy]zinc(II) phthalocyanine}tetraiodide (compound 24);

{2(3),9(10),16(17),23(24)-tetra[N-methyl-2,3,6,7-tetrahydro-1H,5H-pyrido[3,2,1-ij]quinolinium-8-yl)oxy)] phthalocyanine}zinc(II) iodide (compound 25);

2,3,9,10,16,17,23,24-tetra[(N,N'-dimethyl)piperazo]zinc(II) phthalocyanine (compound 26);

2,3,9,10,16,17,23,24-octa[2-(N,N-diethylamino)ethylthio]zinc(II) phthalocyanine (compound 27);

{2,3,9,10,16,17,23,24-octa[3-(N,N,N-trimethylammonium)phenoxy]-dihydroxy Si(IV) phthalocyanine}octaiodide (compound 28);

{2,3,9,10,16,17,23,24-tetra[(N,N,N',N'-tetramethyl)piperazinediiium]zinc(II) phthalocyanine}octaiodide (compound 29);

{2,3,9,10,16,17,23,24-octa[3-(N,N,N-trimethylammonium)phenylthio]zinc(II) phthalocyanine}octaiodide (compound 30);

{2,3,9,10,16,17,23,24-octa[3-(1-methylpiridin-ium)oxy]zinc(II) phthalocyanine}octaiodide (compound 31);

2,3,9,10,16,17,23,24-octa[2-(N,N-dimethylamino)ethylthio]zinc(II) phthalocyanine (compound 32);

{2,3,9,10,16,17,23,24-octa[2-(N,N,N-trimethylammonium)ethylthio]zinc(II) phthalocyanine}octaiodide (compound 33).

5. The pharmaceutical compositions according to claim 1, wherein the said metal chelating agent is selected from the metal chelating agents having specificity for $Ca^{2+}$ and $Mg^{2+}$ ions.

6. The pharmaceutical compositions according to claim 5, wherein the said metal chelating agent is selected from 1,2-diaminocyclohexane-N,N,N',N'-tetraacetic acid (CDTA), diethylenetriamine-pentaacetic acid (DTPA) and ethylenediamine-N,N,N',N'-tetraacetic acid (EDTA).

7. The pharmaceutical compositions according to claim 6, wherein the said metal chelating agent is EDTA.

8. The pharmaceutical compositions according to claim 1, in a formulation selected from solutions, liposome or microvesicle preparations, dispersions, ointments, and other suitable topical dermatological preparations or preparations suitable for in vivo/ex vivo applications.

9. A process for preparing a pharmaceutical composition for photodynamic therapy, said process comprising combining at least a metal phthalocyanine analogue of formula (I) according to claim 1 with at least a metal chelating agent.

10. A method of treating infectious diseases by photodynamic therapy, said method comprising administering to a patient in need of such a treatment a pharmaceutical composition comprising at least a metal phthalocyanine analogue of formula (I) in combination with at least a metal chelating agent according to claim 1.

11. The method according to claim 10, wherein said pharmaceutical composition is administered by topical or parenteral way.

12. The method according to claim 10, wherein said infectious diseases are bacterial, fungal or viral infections.

13. The method according to claim 10, wherein said infectious diseases are skin or mucosal diseases caused by Gram negative bacteria.

14. A method of sterilizing blood or blood derivatives, said method comprising adding to blood or blood derivatives in need of such a treatment a pharmaceutical composition comprising at least a metal phthalocyanine analogue of formula (I) in combination with at least a metal chelating agent according to claim 1, and thereafter irradiating.

15. The pharmaceutical composition according to claim 1, wherein the said metal phthalocyanine analogue is defined by the following formulas:

{2,3,9,10,16,17,23,24-octa[3-(N,N,N-trimethylammonium)phenoxy]zinc(II) phthalocyanine}octaiodide (compound 1);

{2(3),9(10),16(17),23(24)-tetra[1,3-bis-(trimethylammonium)propyl-2-oxy]zinc(II) phthalocyanine}octaiodide (compound 2);

{2(3),9(10),16(17),23(24)-tetra[3-(N,N,N-trimethylammonium)phenoxy]zinc(II) phthalocyanine}tetraiodide (compound 4); and {1(4),8(11),15(18),22(25)-tetra[3-(N,N,N-trimethylammonium)phenoxy]zinc(II) phthalocyanine}tetraiodide (compound 6).

* * * * *

UNITED STATES PATENT AND TRADEMARK OFFICE
CERTIFICATE OF CORRECTION

PATENT NO. : 8,664,382 B2
APPLICATION NO. : 10/512287
DATED : March 4, 2014
INVENTOR(S) : Roncucci et al.

It is certified that error appears in the above-identified patent and that said Letters Patent is hereby corrected as shown below:

On the Title page, Item [73], please delete the name "Molteni Therapeutics S.r.l." and insert as follows: --Molteni Therapeutics S.R.L.--;

In the Claims:
Claim 3, column 16, line 29 the structure should read as follows:

Signed and Sealed this
Tenth Day of June, 2014

Michelle K. Lee
*Deputy Director of the United States Patent and Trademark Office*